United States Patent [19]

Wong

[11] 4,182,884

[45] Jan. 8, 1980

[54] POLYCYCLIC CHLORINATED HYDROCARBONS CONTAINING BRIDGEHEAD OR IMINO NITROGEN

[75] Inventor: John L. Wong, Louisville, Ky.

[73] Assignee: Research Corporation, New York, N.Y.

[21] Appl. No.: 878,794

[22] Filed: Feb. 17, 1978

Related U.S. Application Data

[62] Division of Ser. No. 725,578, Sep. 22, 1976, Pat. No. 4,087,434.

[51] Int. Cl.$^2$ ............................................. C07D 221/22

[52] U.S. Cl. ....................................... 546/72; 546/112; 260/326.11 R

[58] Field of Search ......................... 546/72, 79, 112; 260/326.11 R

[56] References Cited

U.S. PATENT DOCUMENTS

| | | | |
|---|---|---|---|
| 3,647,816 | 3/1972 | Draber et al. | 260/290 HL |
| 4,003,904 | 1/1977 | Adelstein | 546/112 |

*Primary Examiner*—Alan L. Rotman
*Attorney, Agent, or Firm*—Dennis P. Clarke

[57] ABSTRACT

Polycyclic chlorinated amines resulting from cycloadditions useful as insecticides.

2 Claims, No Drawings

POLYCYCLIC CHLORINATED HYDROCARBONS CONTAINING BRIDGEHEAD OR IMINO NITROGEN

This is a division, of application Ser. No. 725,578, filed Sept. 22, 1976 now U.S. Pat. No. 4,087,434, issued May 2, 1978.

BACKGROUND OF THE INVENTION

A well-known class of insecticides includes the polychlorinated cyclic hydrocarbons with endomethylene-bridged structures. Most of these compounds are prepared by the well-known Diels-Alder [4+2] cycloaddition reaction.

The tradenames of various of these insecticides are: Chlordane, Heptachlor, Heptachlor epoxide, Betadihydroheptachlor, Telodrin, Aldrin, Dieldrin, Endrin, Endosulfan (Thiodane), Aldodan, Mirex and Nonachlor.

These insecticides are conventionally used for the control of cockroaches, ants, termites and other household pests, soil insects and a variety of vegetable and field crop pests. They are good contact insecticides whose symptoms of poisoning include disturbance of the ganglia of the central nervous system upon absorption by the insect.

In U.S. applications Ser. Nos. 454,576 (filed Mar. 25, 1974 in the name of Wong, and now abandoned), and 672,322, filed Mar. 31, 1976, there is disclosed a class of compounds possessing an activity similar to the polychlorinated cyclic hydrocarbons. These compounds are, for the most part, the bridgehead nitrogen analogs of the above-noted commercial insecticides. However, they are advantageous in many respects, one being that they are more readily degraded after performing their function thereby lessening the deleterious impact on the environment.

SUMMARY OF THE INVENTION

The present invention relates to a novel class of compounds possessing an insecticidal activity similar to the polychlorinated cyclic hydrocarbons. They usually contain a nitrogen in the ring system. The presence of the hetero-N atom has several favorable effects on the insecticidal function of the compound.

The compounds of the present invention may be prepared by reacting pentachloro-α-pyrrolenine with itself or an appropriate olefin in a cycloaddition reaction, followed by, in some cases, further treatment to yield a desired derivative.

DETAILED DESCRIPTION OF THE INVENTION

The commercial chlorinated hydrocarbon insecticides have been found to be disadvantgeous due to the accumulation of their residues in the environment posing a threat to the general health. As a consequence, the use of the commercial insecticides has been stringently regulated on both the Federal and State levels, thereby severely limiting their applicability. In addition, test colonies have developed widespread resistance to the above-described chlorinated hydrocarbon insecticides, thereby further restricting their applicability.

The polycyclic amines of the present invention lend themselves to relatively easy hydrolysis at the bridgehead nitrogen due to the presence of the N—$CCl_2$ moiety to an amino acid which may be biodegraded further. This biodegradation pathway is unavailable to the above-described commercial insecticides and is highly advantageous in that it solves the notorious residue problem associated with the latter. Also, the lone pair electrons of the nitrogen of these amines will enhance the hydrophilicity as well as the complexation equilibrium constant to the ganglia reception sites via hydrogen bonding. This will have a favorable impact on the transport and the pharmacological effects of the insecticide on the nervous system of the insects.

It has been found that many of the polycyclic amines described in the above-mentioned copending applications are much less toxic than their non-nitrogenous commercial analogs on dermal application to rats. The presence of the hetero nitrogen atom apparently reduces the hazard to users of the insecticides and to wildlife. These advantages, coupled with the fact that the amino analogs differ in structure and properties from the chlorinated hydrocarbons, reduces the problem of build-up pest resistance considerably.

The compounds of the invention may be prepared by cycloaddition reactions employing pentachloro-α-pyrrolenine and the appropriate olefin. The reaction conditions required for producing the required product depend in each case upon the reactants employed. The following non-limiting Examples are set forth to show the methods of preparation of the compounds of the invention.

The reaction of most olefins with pentachloro-α-pyrrolenine produces a reaction product comprising a 1-azapentachlorobicyclo[2.2.1]hept-2-ene nucleus with the substituent attached to the vinyl group in the olefin reactant occupying either the 5 or 6 position. In some instances a mixture of the two regioisomers is produced. It is impossible in some instances to preclude by analysis the existence of one of the regioisomers in the reaction mixture. In each of the following examples a diligent effort was made to correctly characterize the product. It is to be understood, however, by those skilled in the art that the crude reaction product in those examples specifying a single isomer may also additionally contain minor amounts of the regioisomer.

EXAMPLE 1

This Example illustrates the following equation:

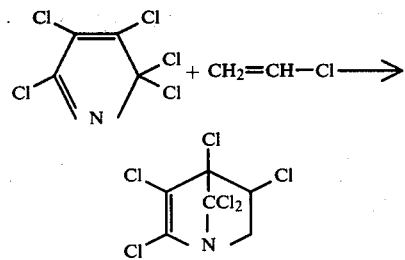

Pentachloro-α-pyrrolenine [1.17 g, 4.9 mmole] and vinyl chloride [0.62 g, 9.9 mmole] were dissolved in 5.6 ml of toluene and heated in a sealed tube at 110° C. for 96 hours. The reaction mixture was decolorized with activated charcoal and the toluene removed in vacuuo. The yellow semi-solid residue was recrystallized from a methylene chloride-pentane mixture to yield 0.78 g (53%) of white crystalline-1-aza-2,3,4,5(endo),7,7-hexachlorobicyclo[2,2,1]hept-2-ene having a m.p. 77°–79° C.; $^1$H NMR δ ($CDCL_3$, δTMS=0) 2.43 (q,J3 Hz,1H), 3.25 (q,J8 Hz, 1H), and 4.70 (q,J3 Hz, 1H).

Anal. Calcd. for C₆H₃N Cl₆: C, 23.84; H, 0.99; N, 4.64. Found: C, 23.80; H, 1.02; N, 4.56.

EXAMPLE 2

A mixture of 2 g (8.4 mmol) of pentachloro-α-pyrrolenine and 0.556 g (8.4 mmol) of cyclopentadiene was allowed to stand at room temperature overnight. The reaction mixture was dissolved in 50% aqueous ethanol and cooled. The precipitate was recovered and sublimed at 55° C., 0.1 mm to yield 1.9 g (74%) of 2-aza-3,3,4,5,6-pentachlorotricyclo[5.2.1.0²·⁶]deca-4,8-diene,

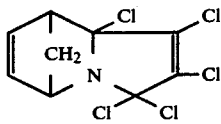

m.p. 173°–174° C.

Anal. Calcd for C₉H₆N Cl₅: C, 35.35;H,1.96;N,4.58. Found: C, 35.36;H,1.94;N,4.46.

A mixture of 5.0 g (16.37 mmol) of the above compound and 3.02 g (17.5 mmol) of m-chloroperbenzoic acid in 25 ml of chloroform was stirred at room temperature for 14 days. The reaction mixture was extracted successively with 3×3 ml of 5% aqueous sodium bisulfite solution and 3×3 ml of 5% aqueous sodium bicarbonate solution. The organic layer was dried, evaporated, and the residue recrystallized three times from ether, yielding 3.40 g of 2-aza-8,9-epoxy-3,3,4,5,6-pentachlorotricyclo[5.2.1.0²·⁶]dec-4-ene, m.p. 90° s; ¹H NMR δ (CDCl₃-TM) 3.62-3.43 (m,2H), 3.23 (m,1H), 2.91 (m,1H), 2.12-1.83 (m,2H):

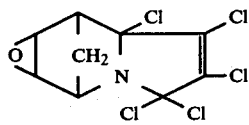

Anal. Calcd for C₉H₆ NOCl₅: C, 33.63; H, 1.88; N,4.36. Found: C, 34.07; H, 2.33; N,4.12.

10 g of the above compound (30 mmole) were heated in 10 one-gram batches in sealed tubes at 140° C. for 17 hours.

The reaction produces a mixture containing substantially equal amounts of the following alcohols a and b:

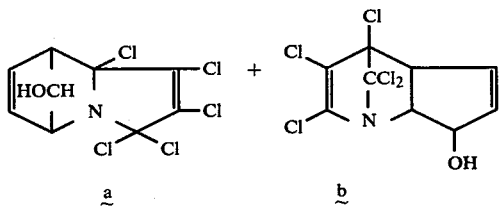

The products may be separated according to the following procedure:

The light brown, gummy residue of each tube was dissolved in separate 20 ml batches of CHCl₃. 0.280 g of active MnO₂ was added to each batch. The heterogeneous reaction mixtures were shaken for two hours, filtered, combined and stripped to dryness. The residue, 9.88 g, was diluted to 10 ml with 95% EtOH and divided into 10 one-ml portions. To each portion was added 10.4 ml of fresh 2,4-dinitrophenylhydrazine (DNP) reagent (20 mg/ml) (0.53 eq). The resulting precipitates were filtered off, washed with 5 ml of cold EtOH and air-dried. The yield was 6.38 g of the dinitrophenylhydrazone of the enone formed by the above oxidation of the mixture of alcohols. The hydrazone was recrystallized 5 times from 95% EtOH, m.p. 251°–252° C., and converted to the enone as shown in the equation below.

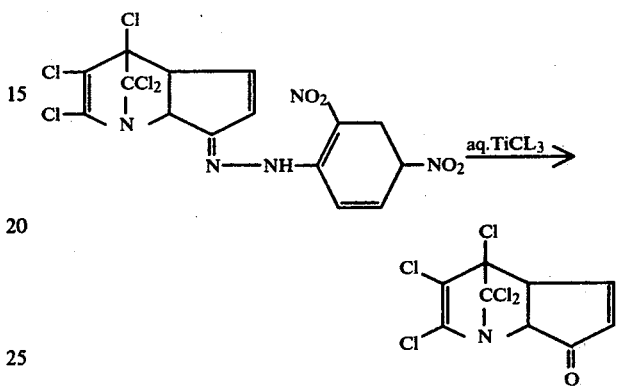

To 0.4995 g (1 mmol) of the above hydrazone in 50 ml of 1,2-dimethoxyethane was added 9.375 ml of 20% aqueous TiCl₃ (15 eq) [J. E. McMurry et al, JOC, Vol. 40, p. 1502 (1975)]. The biphasic mixture was refluxed for 1 hour with stirring. After cooling, 40 ml of H₂O was added and the solution extracted with Et₂O (1×20 ml and 4×10 ml). The ether extracts were dried over MgSO₄ and evaporated to dryness. The crude yield was 0.265 g (82.9%). The solid enone was recrystallized successively from EtOH/H₂O and CH₂Cl₂/pentane and dried at room temperature /0.05 mm Hg over P₂O₅ and paraffin, m.p. 59°–60° C. The product was identified as 1-aza-7,8,9,10,10-pentachlorotricyclo[5.2.1.0²·⁶]-dec-4-en-3-one. This enone was formed when the enol b shown above was oxidized by MnO₂.

IR ν (cm⁻¹ CHCl₃) 3090, 3050, 2990, 2920, 1715, 1620, 154, 1450.

UV λ_max^EtOH 220 nm (E=9320).

¹H NMR δ (CDCl₃/TMS) 6.9 (d, 9 Hz, 1H), 5.8 (m, 1H), 4.1 (d, 8 Hz, 1H). 3.75 (m, 1H).

Anal. Calcd for C₉H₄NOCl₅: C, 33.80; H, 1.25; N, 4.38. Found: C, 33.85; H, 1.79; N, 4.65.

0.4 g of the above enone was dissolved in 20 ml of acetone and photolyzed with a 1200 w high pressure mercury lamp at 20° C. for 12 hours. The product formed was recrystallized from aq. ethanol. M.P. 77°–78°; ¹H NMR (CDCl₃, δ TMS=0)3.5 (m, 2H), 3.88 (m,1H), 4.07 (m, 1H). The "caged" product was identified as 1-aza-2,3,9,10,10-pentachloropentacyclo [5.3.0.0²·⁵.0³·⁹.0⁴·⁸] decan-6-one and having the structural formula:

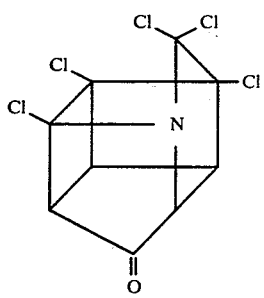

Anal. Calcd for $C_9H_4NOCl_5$: C, 33.80; H, 1.25; N, 4.38 Found: C, 33.39; H, 1.75; N, 4.30

Recovery of the alcohol a is described below. The mother liquor following removal of the dinitrophenylhydrazone precipitate was treated with 2 ml of acetone to remove excess dinitrophenylhydrazine and filtered. The filtrate was stripped down under vacuum, diluted with $H_2O$, neutralized with $NaHCO_3$ and extracted with $CH_2Cl_2$. The extracts were dried over $K_2CO_3$ and stripped to yield 4.5 g of a gummy solid residue which was recrystallized 5 times from $EtOH/H_2O$ and dried at room temperature/0.05 mm Hg over $P_2O_5$, m.p. 99°–100° C. $^1H$ NMR δ ($CDCL_3$/TMS) 6.35 (m,2H), 3.92 (m, 1H), 3.78 (m, 1H), 3.65 (s, 1H exchanges in $D_2O$),3.50 (q, 1H). The product was identified as 2-aza-3,3,4,5,6-pentachlorotricyclo [5.2.1.0$^{2.6}$] deca-4,8,-dien-10-ol having the structural formula:

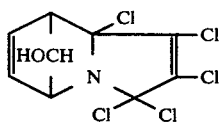

Anal. Calcd for $C_9H_6NOCl_5$: C, 33.59; H, 1.87; N, 4.35. Found: C, 33.40; H, 1.99; N, 4.09.

EXAMPLE 3

This Example illustrates the equation:

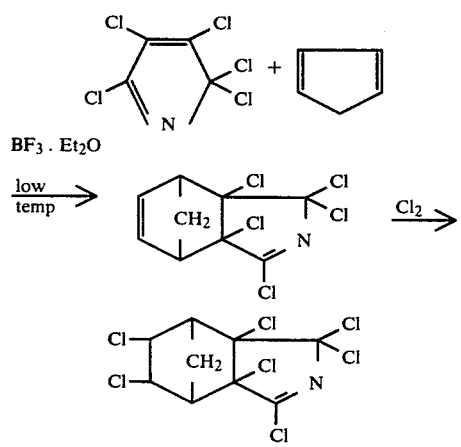

Example 2 describes the reaction between cyclopentadiene and pentachloro-α-pyrrolenine at room temperature. At low temperatures and in the presence of boron trifluoride, the cycloadduct pictured above is produced which cannot be isolated due to its instability at room temperature. It rearranges at room temperature to the cycloadduct obtained when boron trifluoride is not present. This isomeric adduct may be chlorinated, however, to produce a stable product.

Pentachloro-α-pyrrolenine, 5 g (21 mmole),and $BF_3\cdot Et_2O$, 3.58 g (25 mmole), were dissolved in 15 ml of anhydrous ether and stirred for 10 minutes at room temperature. The orange solution was cooled to $-80°$ C. and 1.38 g (21 mmole) of cyclopentadiene was added. After 8 hours the $Et_2O$ was blown off at $-80°$ C. with a stream of $N_2$. The gummy residue was dissolved in 15 ml of $CH_2Cl_2$ containing 1.47 g of $Cl_2$ (28.6 mmole) and the solution was irradiated in a low temperature cell at $-80°$ C. with a GE 300W Reflector Flood Lamp (output primarily at 590mm). The excess $Cl_2$ was allowed to escape and the $CH_2Cl_2$ evaporated under vacuum. The brown oil produced, 6.3 g (98.4%) was molecularly distilled at 50° C./0.03 mm Hg yielding 5.2 g (81%) of a yellow oil. The oil was decolorized with activated charcoal and dried over $K_2CO_3$ in $CHCl_3$. After removal of the $CHCl_3$ under vacuum, there remained 4.85 g (75%) of 4-aza-2,3,5,5,6,8,9-heptachlorotricyclo[5.2.1.0$^{2.6}$]dec-3-ene:

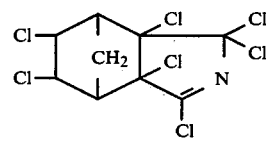

$^1H$ NMR δ ($CDCl_3$-TMS) 4.25 (m, 2H), 2.90 (M. 2H), 2.60 (m, 2H).

IR ν (cm$^{-1}$, smear) 1710 cm$^{-1}$.

UV λ $_{max}^{EtOH}$ 272$_{nm}$ (4520).

Anal. Calcd for $C_9H_6NCl_7$: C, 28.68; H, 1.59; N, 3.72. Found: C, 28.17; H, 1.74; N, 3.63.

EXAMPLE 4

This Example illustrates the equation:

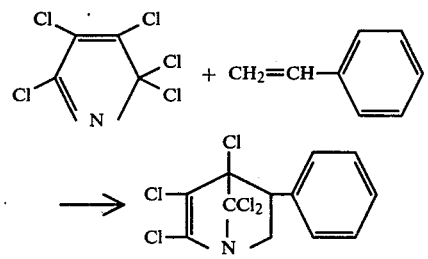

Only one of the two possible regioisomers was found in the product according to glpc analysis. This product was identified as 1-aza-5-phenyl-2,3,4,7,7-pentachlorobicyclo[2.2.1]-2-heptene using nmr method.

In a 25 ml round-bottomed flask equipped with a reflux condenser and a drying tube was placed a 4.92 g (20.5 mmole) of pentachloro-α-pyrrolenine and 2.14 g of styrene (20.5 mmole). The mixture was heated at reflux for 24 hours. The dark brown reaction mixture was decolorized once with activated charcoal, then stripped of solvent and distilled at 130° and 2 mm Hg to give 4.4 g (62%) of a yellow liquid. Upon standing in the freezer ($-20°$ C.) for 24 hours, the clear pale yellow distillate solidified, m.p. 56°–61° C.;

$^1H$ NMR ($CDCl_3$, δ TMS=0) 2.68 (q, 1H), 3.02 (q, 1H), 3.9 (q.14), J=$-14$, 4.6, 9.4 Hz, 7.1–7.5 (m, 5H).

Anal. Calcd for $C_{12}H_8N Cl_5$: C, 41.92; H, 2.35; N, 4.08 Found: C, 41.78; H, 2.56; N, 3.95.

EXAMPLE 5

This Example illustrates the preparation of 1-aza-4,5-benzo-7,8,9,10,10-pentachlorotricyclo[5.2.1.0$^{2.6}$]-8-decene. Only one product was found by glpc analysis in the reaction mixture. Its structure was determined by nmr method.

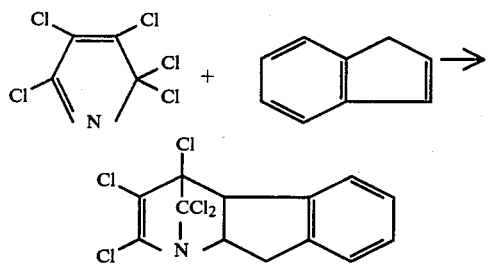

To a solution of indene (1.19 g, 12.5 mmol) in 20 ml of toluene was added 2.46 g (12.5 mmol) of pentachloro-α-pyrrolenine. The mixture was heated at reflux for 24 hours protected from moisture. The red brown reaction mixture was stripped of solvent to give a brown solid which, when recrystallized five times from methylene chloride, gave white crystals (1.98g, 54%), m.p. 130°–131°;

$^1$H NMR (CDCl$_3$, δ TMS=0) 3.1 (m, 2H), 3.68 (m, 1H), 4.36 (d, 1H). J=8 Hz. 7.1–7.5 (m, 4H)

Anal. Calcd for C$_{13}$H$_8$Cl$_5$N: C, 43.92; H, 2.27: N, 3.94 Found: C, 43.65; H, 2.48; N, 3.90

EXAMPLE 6

This Example illustrates the equation:

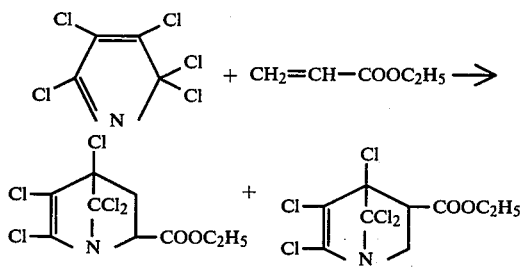

A mixture of two regioisomers in a ratio of 2:1 resulted from this reaction: 1-aza-6-ethoxycarbonyl-2,3,4,7,7-pentachlorobicyclo[2.2.1]hept-2-ene and 1-aza-5-ethoxycarbonyl-2,3,4,7,7-pentachlorobicyclo[2.2.1]hept-2-ene.

In a 100 ml round-bottomed flask equipped with a reflux condenser and a drying tube was placed 15 ml of oxylene, 3.44 g of pentachloro-α-pyrrolenine (14.36 mmol) and 1.44 g (14.35 mmol) of ethyl acrylate. The mixture was heated at reflux for 48 hours at which time there was no evidence (by gas chromatography) of continuing reaction. The reaction mixture was stripped of solvent and the red-brown liquid distilled at 75° and 0.6 mm to give 1.12 g of a pale yellow liquid; $^1$H NMR (CDCl$_3$, δ TMS=0) 3.57–3.65 (m, 1H); 2.58 (d, 2H), 1.31 (t, 3H), J=7H$_z$); 4.24 (q, 2H, J=7H$_z$).

Anal. Calcd for C$_9$H$_8$Cl$_5$NO$_2$: C, 31.81; H, 2.36; N, 4.12. Found: C, 31.59; H, 2.46; N, 4.07.

EXAMPLE 7

The Example illustrates the equation:

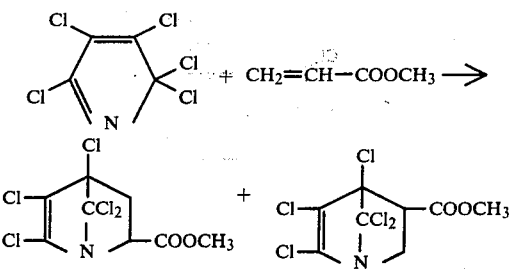

A mixture of two regioisomers in a ratio of 2.2:1 resulted from this reaction. The major isomer was determined to be 1-aza-6-methloxycarbonyl-2,3,4,7,7-pentachlorobicyclo [2.2.1]hept-2-ene and the minor isomer 1-aza-5-methloxycarbonyl-2,3,4,7,7-pentachlorobicyclo[2.2.1]hept-2-ene by means of nmr spectroscopy. They were separated by recrystallization.

In a 10 ml round-bottom flask equipped with a reflux condenser and a drying tube was placed 4.92 g of pentachloro-α-pyrrolenine (20.5 mmol) and 1.76 g methyl acrylate (20.5 mmol). The mixture was heated at reflux for 48 hours at which time there was no evidence by gas chromatography of continuing reaction. The red-brown liquid was distilled at 120° C. and 0.8 mm to give a pale orange distillate which solidified upon standing at −20° C. The solid mixture was recrystallized four times from methylene chloride-pentane to yield pure 6-methoxycarbonyl isomer in the precipitate, m.p. 57°–61°, and the minor 5-methoxycarbonyl isomer in the mother liquor.

$^1$H NMR (CDCL$_3$, δ TMS=0) 6-methoxycarbonyl isomer: 2.47 (q, 1H); 2.62 (q, 1H); 3.51 (q, 1H), J= −13.3, 4.7, 9.3 Hz, 3.80 (s, 3H) 5-methoxycarbonyl isomer: 2.80 (q, 1H), 2.93 (q, 1H), J= −13.3, 4.0, 9.0 Hz, 3.77 (s, 3H).

Anal. Calcd for C$_8$H$_6$Cl$_5$NO$_2$: C, 29.49; H, 1.89; N, 4.30. Found: C, 29.16; H, 2.18; N, 4.24.

EXAMPLE 8

This Example illustrates the preparation of 1-aza-5-octyl-2,3,4,7,7-pentachlorobicyclo [2.2.1]hept-2-ene. Only one product was found by glpc analysis.

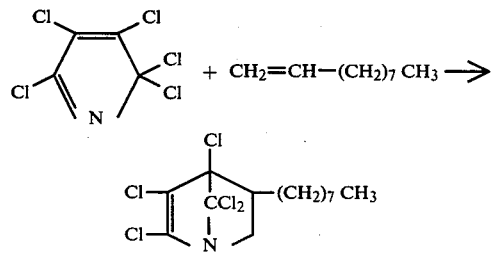

In a glass tube was placed 0.492 g (2.05 mmol) of pentachloro-α-pyrrolenine and 0.292 g of 1-decene (2.05 mmol). The tube was sealed under vacuum and heated to 140° C. for 40 hours. The dark brown liquid was distilled at 1.2 mm. and 95°–120° C. (oil bath temperature) to give a clear colorless liquid.

Anal. Calcd for C$_{14}$H$_{20}$Cl$_5$N: C,44.16; H, 5.33; N, 3.70. Found: C,44.18; H, 5.26; N, 3.68.

EXAMPLE 9

This Example illustrates the equation:

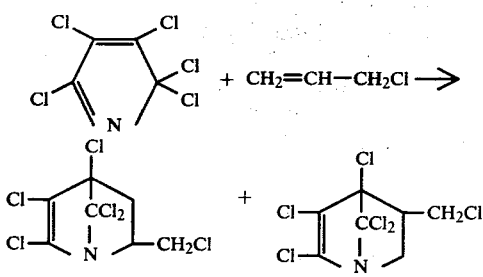

A mixture of two regioisomers in a ratio of 1:1 resulted from this reaction: 1-aza-6-chloromethyl-2,3,4,7,7-pentachlorobicyclo[2.2.1]hept-2-ene and 1-aza-5-chloromethyl-2,3,4,7,7-pentachlorobicyclo[2.2.1]hept-2-ene. The latter compound was isolated pure by precipitation.

In a 100 ml round-bottomed flask was placed 3.44 g of pentachloro-α-pyrrolenine (14.34 mmol) and 1.10 g of 3-chloropropene (14.34 mmol) in 35 ml toluene. The mixture was heated at reflux for 48 hours. The solution was evaporated and the residual brown liquid was distilled at 110° C. and 0.3 mm. The pale yellow distillate partially crystallized upon standing at 25°. The solid precipitate was shown by nmr to be the 5chloromethyl compound, m.p. 88°-93°;

$^1$H NMR (CDCL$_3$, δ TMS=0) 5-chloromethyl isomer: 3.77 (m, 1H) 2.11 (q, 1H); 2.84 (q, 1H); 3.13 (m, 2H), J=−12.7, 3.3 Hz, 6-chloromethyl isomer: 1.89 (q, 1H), 2.6 (q, 1H), 3.93 (q, 1H), 3.16 (m, 2H).

Anal. Calcd for C$_7$H$_5$Cl$_6$N: C, 26.62; H, 1.60; N, 4.43. Found: C, 26.56; H, 1.93; N, 4.45.

EXAMPLE 10

The Example illustrates the preparation of 1-aza-5(4-chlorophenyl)-2,3,4,7,7-pentachlorobicyclo[2.2.1]-hept-2-ene. Only one product was formed by glpc analysis.

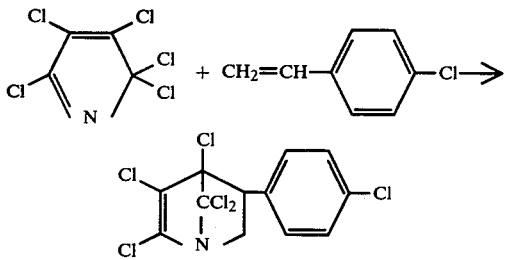

In a 25 ml round-bottomed flask equipped with a reflux condenser and a drying tube was placed 4.92 g of pentachloro-α-pyrrolenine (20.5 mmol) and 2.78 g of para-chlorostyrene (20.5 mmol). The mixture was heated in an oil bath at 140° C. for 26 hours. The brown solid which formed as the reaction vessel was cooled and decolorized once with activated charcoal and recrystallized four times from methylene chloride to give white crystals. m.p. 164°-166° C.;

$^1$H NMR (CDCl$_3$, δ TMS=0) 2.62 (q, 1H); 3.03 (q, 1H), 3.88 (q, 1H), J=−13.4, 4.6, 9.4 Hz, 7.05–7.4 (m, 4H)

Anal. Calcd for C$_{12}$H$_7$Cl$_6$N: C, 38.14; H, 1.87; N, 3.71. Found: C, 38.01; H, 1.88; N, 3.86.

EXAMPLE 11

This Example illustrates the preparation of 1-aza-5-ethoxy-2,3,4,7,7-pentachlorobicyclo[2.2.1]hept-2-ene.

No other isomer could be isolated from the reaction product.

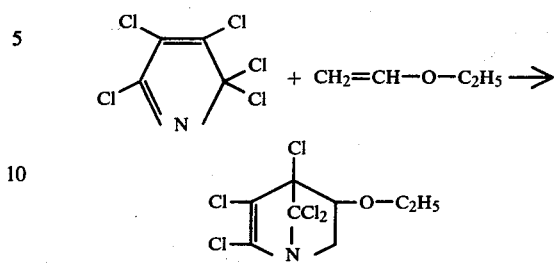

In a 25 ml round-bottomed flask equipped with a reflux condenser and a drying tube was placed 492 mg of pentachloro-α-pyrrolenine (2.05 mmol) and 148 mg of ethyl vinyl ether (2.05 mmol) in 5 ml of benzene. The mixture was heated at reflux for 50 hours at which time there was no evidence of continuing reaction. The light brown reaction mixture was stripped of its solvent with a rotary evaporator. The residue chromatographed on a silica gel column and eluted with chloroform-hexane giving 158 mg of a white solid, m.p. 43°-6° C.

$^1$H NMR (CDCl$_3$, δ TMS=0) 1.16 (t, 3H), 3.7 (m, 2H), J=7.5 Hz, 2.14 (q, 1H), 2.96 (q, 1H), 4.38 (q, 1H), J=2.5,−13, 7.5 Hz.

Anal. Calcd for C$_8$H$_8$Cl$_5$N; C, 32.55; H, 2.72; N, 4.74. Found: C, 32.50; H, 2.54; N, 5.10.

EXAMPLE 12

This Example illustrates the preparation of 1-aza-5-(4-methoxyphenyl)-2,3,4,7,7-pentachlorobicyclo[2.2.1-]hept-2-ene. Only one regioisomer was found in the reaction product.

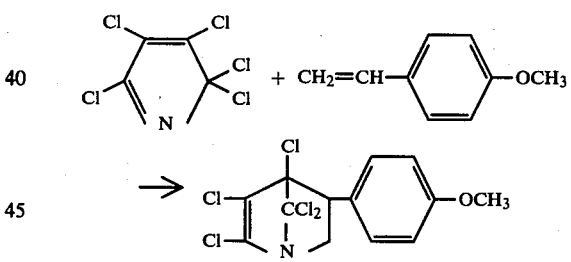

In a 25 ml round-bottomed flask equipped with a reflux condenser and a drying tube were placed 492 mg of pentachloro-α-pyrrolenine (2.05 mmol) and 275 mg of 4-vinylanisole (2.05 mmol) in 5 ml of benzene. The mixture was heated at reflux for 31 hours. The dark brown reaction mixture was stripped of solvent with a rotary evaporator and the product was distilled at 1 mm and 120° C. to give a clear pale yellow liquid which solidified after standing at −20° C. overnight. M.P. 79°-80° C.; $^1$H NMR (CDCl$_3$, δ TMS=0) 2.60 (q, 1H), 2.99 (q, 1H), 3.80 (q, 1H). J=−13, 6.0, 11.5 Hz. 3.77 (s, 3H), 6.7–7.25 (m, 4).

Anal. Calcd for C$_{13}$H$_{10}$Cl$_5$N: C, 41.77; H, 2.68; N, 3.75. Found: C, 42.07; H, 2.81; N, 3.53.

EXAMPLE 13

This Example illustrates the preparation of 1-aza-5,5-dimethyl-2,3,4,7,7-pentachlorobicyclo[2.2.1]hept-2-ene. Only one regioisomer was found in the reaction product.

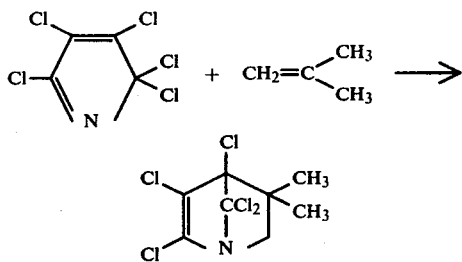

A mixture of 492 mg of pentachloro-α-pyrrolenine (2.05 mmol) and 0.5 g of condensed isobutylene in a sealed thick-walled glass tube was heated at 100° C. for 72 hours. The reaction mixture was evaporated and chromatographed on silica gel eluted with chloroform-isooctane. The eluent was decolorized and evaporated to give 206 mg of a white solid, m.p. 95°–99° C.; $^1$H NMR (CDCl$_3$ δ TMS=0) 1.12 (s, 3H), 1.51 (s, 3H), 2.17 (d, 1H), 2.68 (d, 1H). J=−14 Hz.

Anal. Calcd for C$_8$H$_8$Cl$_5$N: C, 32.53; H, 2.73; N, 4.74. Found: C, 32.71; H, 2.73; N, 4.67.

EXAMPLE 14

This Example illustrates the preparation of 1-aza-5-methyl-2,3,4,7,7-pentachlorobicyclo[2.2.1]hept-2-ene which was the major regioisomer found in the reaction product.

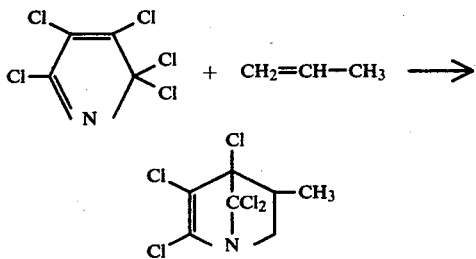

Following the procedure of Example 13 pentachloro-α-pyrrolenine and propene-1 were reacted to yield the above product, m.p. 90°–93° C.; $^1$H NMR (CDCl$_3$, δ TMS=0) 1.11 (d, 3H, J=6.7 Hz), 1.44–2.0 (m, 1H), 2.48–3.04 (m, 2H).

Anal. Calcd for C$_7$H$_6$Cl$_5$N: C, 29.88; H, 2.15; N, 4.98. Found: C, 29.64; H, 2.29; N, 4.87.

EXAMPLE 15

This Example illustrates the preparation of 1-aza-5-methyl-5-phenyl-2,3,4,7,7-pentachlorobicyclo[2.1.1-]hept-2-ene. Only one product was found according to glpc analysis.

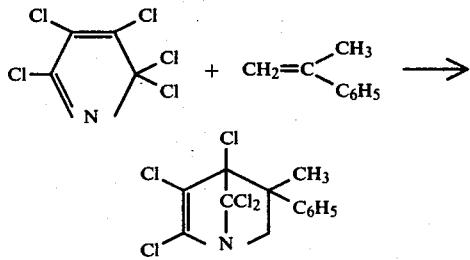

A mixture of 2.46 g (10.3 mmol) of pentachloro-α-pyrrolenine and 1.21 g (10.3 mmol) of α-methylstyrene in 20 ml of toluene was refluxed for 42 hours. The mixture was evaporated and chromatographed on silica gel with hexane to yield 341 mg of a white solid, m.p. 75°–79° C.; $^1$H NMR (CDCL$_3$, δ TMS=0) 1.96 (s, 3H), 7.2–7.6 (m, 5H), 2.79 (d, 1H); 3.35 (d, 1H). J=−14 Hz.

Anal. Calcd for C$_{13}$H$_{10}$Cl$_5$N: C, 43.72; H, 2.82; N, 3.91. Found: C, 43.71; H, 2.91; N, 3.92.

EXAMPLE 16

This Example illustrates the preparation of 1-aza-2,3,4,7,7-pentachlorobicyclo[2.2.1]hept-2-ene.

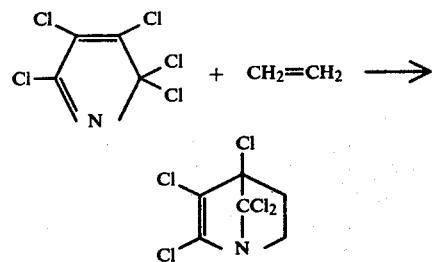

Following the procedure of Example 13 pentachloro-α-pyrrolenine and ethylene were reacted to yield a white solid, m.p. 66°–71° C.; $^1$H NMR (CDCl$_3$, δ TMS=0), 1.954 (m, 1H), 2.474 (m, 1H), 2.192 (m, 1H), 2.617 (m, 1H).

Anal. Calcd for C$_6$H$_4$Cl$_5$N: C, 26.95; H, 1.51; N, 5.25. Found: C, 26.82; H, 1.96; N, 5.10.

EXAMPLE 17

This Example illustrates the equation:

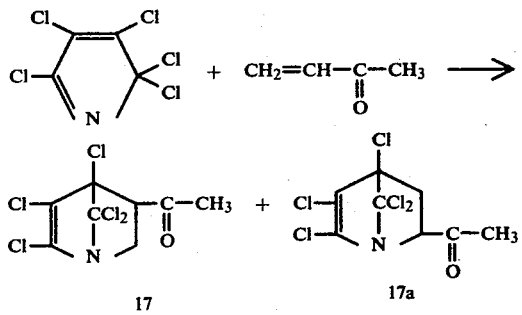

17          17a 1-aza-5-methylcarbonyl-2,3,4,7,7-pentachlorobicyclo [2.2.1]-2-heptene (17). 1-aza-6-methylcarbonyl-2,3,4,7,7-pentachlorobicyclo[2.2.1-2-heptene (17a). To 5 ml of distilled toluene contained in a 25 ml round-bottomed flask was added 0.492 g of pentachloro-6α -pyrrolenine (0.00205 mol) and 0.144 g of methyl vinyl ketone (0.00205 mol). The mixture was heated at reflux for 48 hours. The dark brown reaction mixture was cooled to room temperature and stripped on a rotary evaporator. The remaining material was dissolved in 1 ml of hexane and eluted through an 11 m glass column packed with 50 g of silica gel in hexane. The eluent containing the major product (retention time 1.8 min, T$_c$=175°) was stripped off to give 0.0682 g (10.7%) of a white solid (17), M.P. 95°–99°. The eluent containing the minor product (retention time 2.2 min, T$_c$=175°) was stripped off to give 0.016 g (2.5%) of an off-white solid (17a); $^1$H NMR (17) δ 2.47 (q, 1H), 2.47 (s, 3H), 2.80 (q, 1H), 3.72 (q, 1H). J=−13, 8.5, and 4.0 H$_z$.

Anal. Calcd for $C_8H_6NCl_5$: C, 31.06; H, 1.95; N, 4.53. Found: C, 31.00; H, 1.96; N, 4.56.

EXAMPLE 18

This Example illustrates the equation:

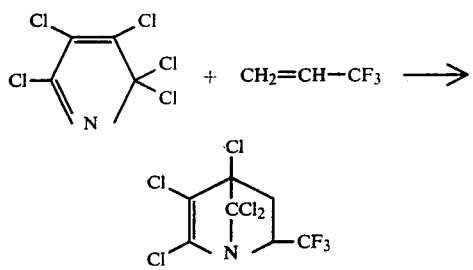

The above regioisomer was found in the reaction mixture as the major reaction product. Minor amounts of the 5-trifluoromethyl isomer were also found.

1-aza-6-trifluoromethyl-2,3,4,7,7-pentachlorobicyclo[2.2.1]2-heptene.

To approximately 0.5 g (0.0052 mmol) of 3,3,3-trifluoropropene condensed at −78° in a heavy-walled glass tube was added 0.492 g of pentachloro-α-pyrrolenine. The tube was sealed under vacuum and heated in an oven at 165° C. for 65 hours. The tube containing the clear, dark brown reaction mixture was cooled in dry ice/acetone prior to opening, the afterwards was warmed slowly to room temperature. The remaining dark liquid was dissolved in 1 ml of hexane and eluted through an 11 mm glass column packed with 50 g of silica gel in hexane. The polarity of the eluent was increased to 3:1 hexane: chloroform until the product was collected. The eluent containing the product was filtered through a 0.45 micron millipore filter and evaporated on a rotary evaporator to give 0.058 g (8.4%) of a pale yellow liquid which solidified on standing for one hour at −20° C.

Anal. Calcd for $C_7H_3NF_3Cl_5$: C, 25.07; H, 0.90; N, 4.18. Found: C, 24.86; H, 0.93; N, 4.05.

$^1$H NMR δ 2.16 (q), 2.79 (q), methylene H.

EXAMPLE 19

This Example illustrates the preparation of a diazadecachloro caged compound or dimer of pentachloro-α-pyrrolenine having the structural formula:

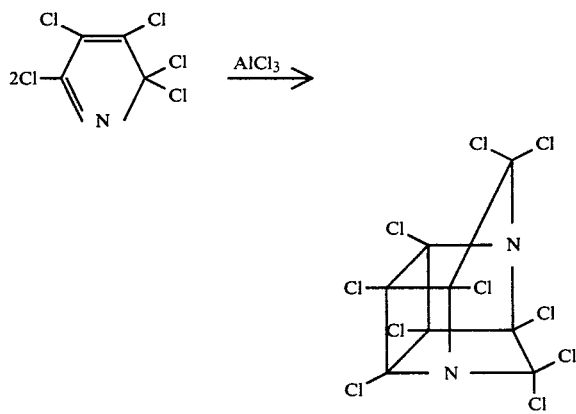

10 g of penachloro-α-pyrrolenine (PCP) (42 mmol) was refluxed in 100 ml of $CCl_4$ for five days in the presence of 1.11 g of $AlCl_3$ (84 mmol). The solution was extracted with water, dried, concentrated, and chromatographed on a silica gel column and eluted with pentane. 4.65 g of the starting pyrrolenine was recovered. the product (4.55 g) was eluted with acetone and decolorized with charcoal to give 4.3 g of a white solid.

UV ($Et_2O$): end absorption; after standing at 25°: λ max 282(1015), equivalent to 99.1% regeneration of pentachloro-α-pyrrolenine (PCP).

MW ($\phi_2O$ freezing point depression) determination:

|  | Calcd. | Found |
|---|---|---|
| PCP | 239.5 | 252.6 |
| Dimer | 479 | 505 | mp 127°–133° (DSC, 20°/min scanning)
IR ($CCl_4$, $cm^{-1}$, all major bands)
  Mirex: 655, 1058, 1130, 1145.
  Dimer: 655, 1058, 1128, 1145, 1152, 1172.
Stability: $T_{\frac{1}{2}}$ (25°) 9 days.

This dimer also forms a stable complex with two equivalent of $AlCl_3$ in $CCl_4$.

Characterization of $AlCl_3$ complex of dimer is as follows:

UV ($CCl_4$): 515 nm (E=3475)
IR ($CCl_4$, $cm^{-1}$):
  Dimer: 655, 1058, 1128, 1145, 1152, 1172
  Dimer - 2 $AlCl_3$ complex: 450, 650, 660, 1160, 1128, 1145, 1155, 1200

Stability: Stable at 25° C. indefinitely. The favored structure of this dimer product is 1,4-diaza-2,3,3,5,6,7,8,9,10,10-decachloropentacyclo[5.3.0.0$^{2.6}$.0.$^{4.9}$.0.$^{5.8}$]decane as shown.

Correct combustion analysis, chromatographic or spectral characterization were obtained for all compounds. Ir spectra were run on Beckman IR-12, Nmr spectra were determined with the Varian A-60 instrument, using tetramethylsilane as internal reference (δ0). Glpc analyses were performed on a Hewlett Packard 5750B chromatograph with dual flame ionization detector. All analyses were done on a 10 ft.×0.125 in. aluminum column packed with 20% SE-30 on Chromosorb W AW DMCS and at 30 cc/min of nitrogen, $T_1$=270°, $T_D$−240°, $T_C$=170° (unless otherwise noted). High pressure liquid chromatography was done on Waters Associates instrument using 1 ft. μ-porasil column, 254 nm uv detector, and chloroform at 0.6 ml/min. Melting points are uncorrected.

It is to be understood that all of the above structural formulas and names of products were deduced from the analytical data set forth. This is not to preclude the possibility, however, of structures other than those depicted. It is to be understood that the invention includes the compounds and reaction mixtures produced according to the methods set forth in the above Examples and described elsewhere in the specification.

EXAMPLE 20

Several of the compounds of the above examples were tested for their insecticidal activity against a variety of insects. The insects treated, the method of treatment and the solutions employed are set forth in Table 1.

TABLE 1

| ORGANISM | TEST METHOD | TEST SOLUTION** |
|---|---|---|
| Housefly | Contact spray | 500 ppm in acetone |
| German cockroach | Contact spray | 500 ppm in acetone |
| American cockroach | Contact spray | 500 ppm in acetone |
| Alfalfa weevil | Contact spray | 500 ppm in acetone |
| Cotton aphid | Leaf dip* | 40 ppm - acetone + adjuvant dispersed in water |
| 2-Spot Mite | Leaf dip* | 40 ppm - acetone + adjuvant dispersed in water |
| Mite eggs | Leaf dip* | 40 ppm - acetone + adjuvant dispersed in water |
| Cabbage looper | Leaf dip | 500 ppm - acetone + adjuvant dispersed in water |
| Mock colorado potato beetle | Leaf dip | 500 ppm - acetone + adjuvant dispersed in water |
| Tobacco budworm | Leaf dip | 500 ppm - acetone + adjuvant dispersed in water |
| Housefly larvae | Soil mix | 2400 ppm - acetone + adjuvant dispersed in water |
| Aphid | Soil drench | 80 ppm - acetone + adjuvant dispersed in water |
| Aphid | Foliage spray Potted plant | 2000 ppm - acetone + adjuvant dispersed in water |
| Alfalfa weevil | Foliage spray Potted plant | 2000 ppm - acetone + adjuvant dispersed in water |
| Housefly | Cardboard surface spray | 18.75 mg/6 ml - kerosene:acetone 1:1 |
| Argentine ant | Cardboard surface spray | 6 mg/6 ml - kerosene:acetone 1:1 |

*Infested prior to dip
**Screen dose given, continued with serial dilutions when active The results of the test are set forth in Table 2.

TABLE 2

| Compound Example Number | AFALFA WEEVIL ADULT | HOUSE-FLY ADULT | AMERICAN COCKROACH NYMPH | GERMAN COCKROACH ADULTS | TOBACCO BUDWORM LARVAE | CABBAGE LOOPER LARVAE | MOCK COLORADO POTATO BEETLE 2nd Stg. Larva | 7-DAY EXPOSURE HOUSEFLY LARVAE SOIL TREATMENT | COTTON APHID ADULT | PARATHION-RESISTANT TWO-SPOTTED SPIDER MITE LEAF DIP | |
|---|---|---|---|---|---|---|---|---|---|---|---|
| | | | CONTACT SPRAY LD$_{90}$, or % CONTROL at PPM* | | LEAF FEED LD$_{90}$, or % CONTROL at PPM* | | | LD$_{90}$, or % C* at PPM | LD$_{90}$, or % C* at PPM | LD$_{90}$, or % Control at PPM* | |
| | | | | | | | | | | EGG | ADULT |
| Ex. 3 | 170 | 83 at 100 | 190 | 45 at 500 | 450 | 26 at 500 | <32 | 30 | NA | 31 at 40 | NA |
| Ex. 4 | NA | 10 at 100 | NA | NA | 66 at 500 | NA | 50 at 500 | 43 at 40 | NA | 77 at 40 | NA |
| Ex. 7 | NA | 26 at 100 | NA | NA | 13 at 500 | NA | NA | 13 at 40 | 36 at 10 | NA | NA |
| Ex. 5 | NA | 42 at 100 | NA | NA | 6 at 500 | NA | NA | 47 at 40 | NA | 13 at 40 | NA |
| Ex. 19 | NA | 73 at 100 | 15 at 250 | NA | NA | NA | NA | 47 at 40 | 10 | 21 at 40 | NA |
| STD. | METHYL-PARA-THION 36 | DIBROM 9.4 | DIAZINON 54 | DIAZINON 118 | METHYL PARA-THION 44 | METHYL PARA-THION 15 | METHOXY-CHLOR <32 METHYL-PARA-THION 12.8 | DIAZINON 10  67 at 40 / 37 at 40 | DIBROM 3.0 | TEDION 0.45 | DIBROM 25 |

*LD$_{90}$ values underlined; % control not underlined
NA - not active

What is claimed is:
1. A mixture of compounds of the formulae:
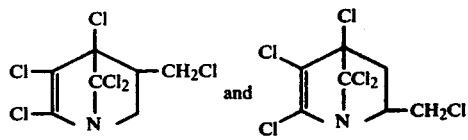
2. A compound of the formula selected from the group consisting of
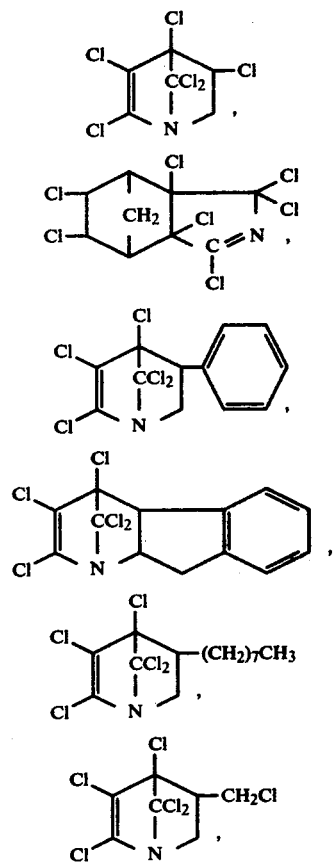
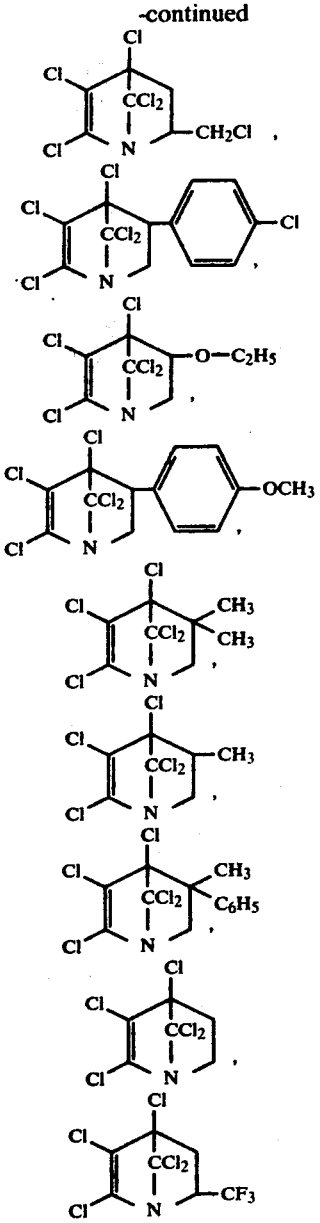
* * * * *